United States Patent [19]
Inman et al.

[11] Patent Number: 5,497,788
[45] Date of Patent: Mar. 12, 1996

[54] WOUND CLOSURE DEVICE FOR VIEWING A WOUND AND METHOD

[75] Inventors: J. D. Inman, Santa Barbara, Calif.; C. E. Ward, Jr., Grand Prairie, Tex.

[73] Assignee: Tecnol Medical Products, Inc., Fort Worth, Tex.

[21] Appl. No.: 278,575

[22] Filed: Jul. 20, 1994

Related U.S. Application Data

[63] Continuation of Ser. No. 92,594, Jul. 16, 1993, abandoned.
[51] Int. Cl.⁶ .................................................... A61F 13/00
[52] U.S. Cl. ........................................ 128/888; 602/43
[58] Field of Search .................................. 128/849–856, 128/888; 602/41, 42, 43, 47, 52, 57

[56] References Cited

U.S. PATENT DOCUMENTS

| | | | |
|---|---|---|---|
| 3,645,835 | 7/1969 | Hodgson | 161/146 |
| 3,918,446 | 11/1975 | Buttarvoli | 604/180 |
| 4,096,863 | 6/1978 | Kaplan et al. | 128/349 R |
| 4,165,748 | 8/1979 | Johnson | 128/348 |
| 4,275,721 | 6/1981 | Olson | 604/180 |
| 4,450,845 | 5/1984 | Engel | 128/854 |
| 4,583,976 | 4/1986 | Ferguson | 604/174 |
| 4,614,183 | 9/1986 | McCracken et al. | 128/132 R |
| 4,641,643 | 2/1987 | Greer | 128/888 |
| 4,669,458 | 6/1987 | Abraham et al. | 128/DIG. 26 |
| 4,678,462 | 7/1987 | Vaillancourt | 604/180 |
| 4,704,177 | 11/1987 | Vaillancourt | 604/180 |
| 4,838,868 | 6/1989 | Forgar et al. | 604/180 |
| 4,875,896 | 10/1989 | Kurtz | 604/187 |
| 4,898,587 | 2/1990 | Mera | 604/180 |
| 4,907,579 | 3/1990 | Kum | 128/888 |
| 4,917,112 | 4/1990 | Kalt | 128/888 |
| 5,012,801 | 5/1991 | Feret | 128/888 |
| 5,092,323 | 3/1992 | Riedel | 128/888 |
| 5,116,324 | 5/1992 | Brierley et al. | 604/180 |
| 5,127,423 | 7/1992 | Draeger | 128/849 |
| 5,170,781 | 12/1992 | Loomis | 128/888 |
| 5,181,914 | 1/1993 | Zook | 128/888 |
| 5,197,493 | 3/1993 | Grier-Idris | 128/853 |
| 5,282,791 | 2/1994 | Lipton | 604/180 |

*Primary Examiner*—Michael A. Brown
*Attorney, Agent, or Firm*—Baker & Botts

[57] ABSTRACT

A unitary wound closure device adapted to permit a wound on a patient to be viewed while the closure device is secured to the patient. The device includes a body having sufficient flexibility for it to be folded against itself. The body includes first and second surfaces facing away from one another, a securing portion having a length and width sufficient to secure facing edges of the wound in close juxtaposition with one another and a viewing portion having a length and width sufficient to circumscribe the wound on the patient. A first quantity of adhesive substance is disposed on the first surface of the body to adhere the securing portion of the body to the patient. A second quantity of adhesive substance is disposed on the second surface of the body to adhere the viewing portion to the patient and the securing portion when the viewing portion is folded over and onto the protecting portion and the patient. A method of protecting and viewing a wound in a patient that comprises positioning the edges of the wound in close juxtaposition relation to one another. A securing portion of a flexible material is then adhered to the patient with the edges of the wound in close juxtaposition. A viewing portion of the flexible material is folded over the securing portion of the flexible material.

14 Claims, 1 Drawing Sheet

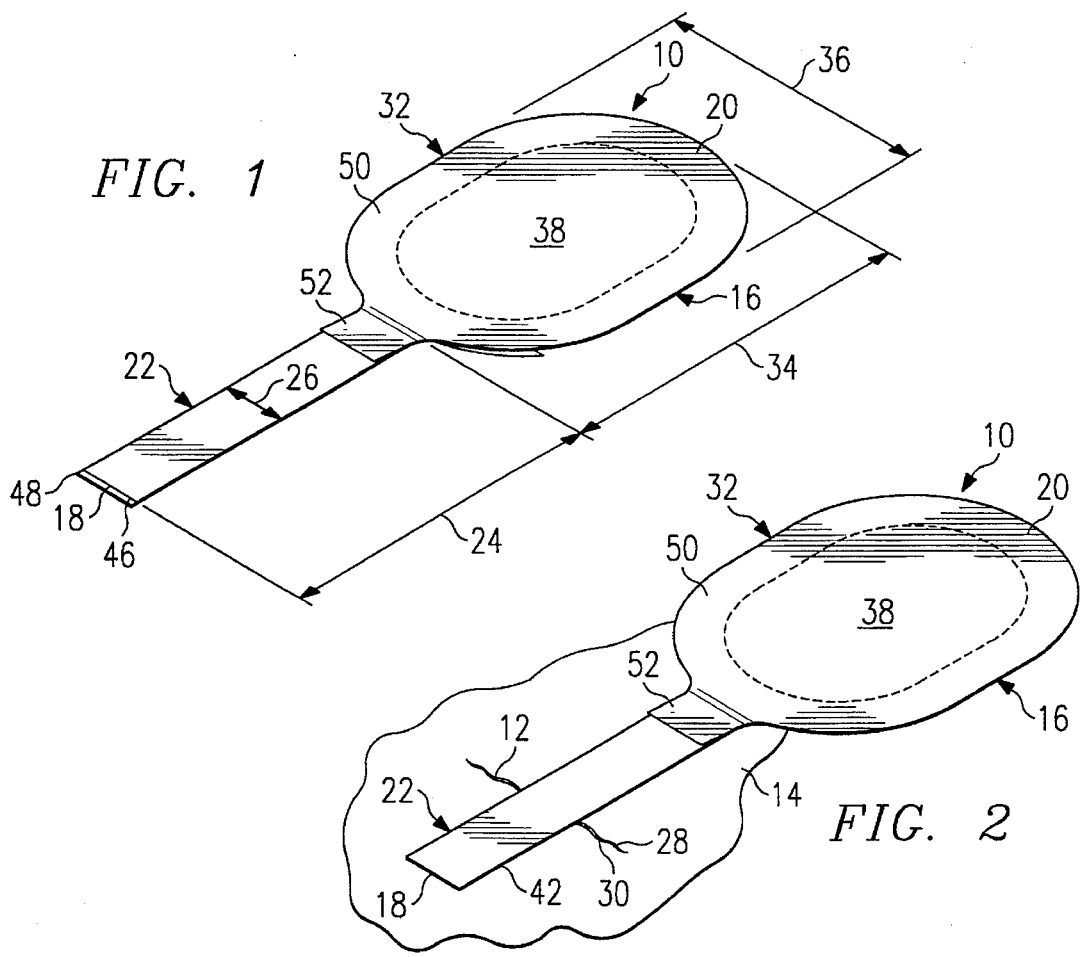
FIG. 1
FIG. 2
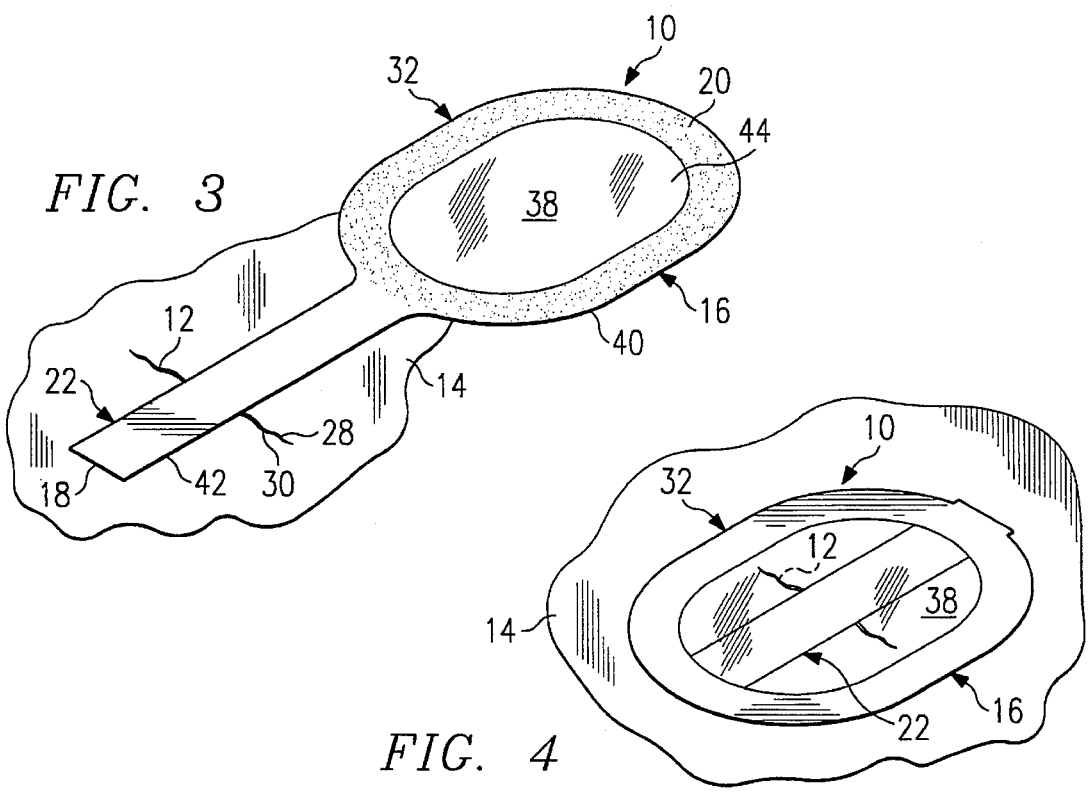
FIG. 3
FIG. 4

WOUND CLOSURE DEVICE FOR VIEWING A WOUND AND METHOD

CROSS REFERENCE TO RELATED APPLICATION

This application is a continuation of application Ser. No. 08/092,594, filed Jul. 16, 1993, entitled "Wound Closure Device For Viewing a Wound and Method" by J. C. Inman and C. E. Ward, Jr., now abandoned.

TECHNICAL FIELD

This invention relates to a unitary device to close a wound on a patient and adapted to permit the wound to be viewed while such device is secured to the patient and method, and; more particularly, to an adhesive device for closing a wound on a patient and for viewing the wound while such device is secured to the patient and method.

BACKGROUND ART

The use of a transparent adhesive film dressing to prevent bacteria from invading the wound and help reduce the risk of infection is well known.

An example of such a dressing is given by Robert W. McCracken, et al., in U.S. Pat. No. 4,614,183, issued on Sep. 30, 1986. This patent discloses an adhesive film dressing in which the adhesive is provided along a surface of the dressing and the adhesive is covered by three release papers. This transparent dressing includes flaps on the release papers in close relation with one another, which interferes with an individual attempting to remove the release papers. Further, the dressing is of such size as to make it difficult, if not impossible, to insure the edges of a wound on the patient are in close juxtaposition should the dressing be used as a wound closure device.

It is also well known to use a wound closing device with a transparent portion to view the wound site to accomplish this result. One example of this device is sold under the name Steri-Strip™, Laparoscopic Wound Closure System featuring Tegaderm™ Transparent Dressing and made by the Medical-Surgical Division-3M Health Care, which is licensed under U.S. Pat. No. 3,645,835. This prior art device is a two piece arrangement with one piece being a slender strip and the other piece being generally oval with tabs on each end. The slender strip is of a first material and is used to close the wound and keep the edges of the wound in juxtaposition. The oval piece is made from of a second material, pressure-sensitive adhesive, and is secured to the patient after release paper is removed from the pressure-sensitive adhesive. The paper backing covers the other side of the oval piece and is removed after the oval piece is secured to the patient. The slender strip is secured to the side of the paper backing, which is disposed on the side away from the release paper, and retains a part of the paper backing in place. This part protects the pressure-sensitive adhesive until removed, after which the oval piece is positioned on the patient. Should the slender strip of this prior art wound closure device be separated from the oval piece and lost, the device is inoperable. Further, the removal of the paper backing prior to the release paper being removed, the device cannot be used. Further, since the two pieces are made from different material, the assembly of the component parts must be made and such assembly is difficult.

Accordingly, it is an object of the present invention to provide a unitary wound closure device adapted to permit a wound on a patient to be viewed while the closure device is secured to the patient.

Further, it is an object of the present invention to provide a unitary wound closure device that enables the health care provider to not remove their rubber gloves when securing a surgical instrument to a patient.

Further, it is an object of the present invention to provide a unitary wound closure device that is easier to use and less likely to become inoperable when component parts are removed than prior art devices.

Further, it is an object of the present invention to provide a method of protecting and viewing a wound in a patient.

DISCLOSURE OF THE INVENTION

In accordance with the present invention, there is provided a unitary wound closure device adapted to permit a wound on a patient to be viewed while the closure device is secured to the patient. The device comprises a body having sufficient flexibility for it to be folded against itself. The body includes first and second surfaces facing away from one another, a securing portion having a length and width sufficient to secure facing edges of the wound in close juxtaposition with one another and a viewing portion having a length and width sufficient to circumscribe the wound on the patient. A first quantity of adhesive substance is disposed on the first surface of the body to adhere the securing portion of the body to the patient. A second quantity of adhesive substance is disposed on the second surface of the body to adhere the viewing portion to the patient and the securing portion when the viewing portion is folded over and onto the protecting portion and the patient.

Further, in accordance with the present invention there is provided a method of protecting and viewing a wound in a patient that comprises positioning the edges of the wound in close juxtaposition relation to one another. A securing portion of a flexible material is then adhered to the patient with the edges of the wound in close juxtaposition. A viewing portion of the flexible material is folded over the securing portion of the flexible material. The viewing portion of the elongated flexible material is adhered to the patient and the securing portion of the flexible material to permit the wound to be viewed.

BRIEF DESCRIPTION OF THE DRAWINGS

Other objects and advantages of the invention will become apparent upon reading the following detailed description and upon reference to the drawings, wherein like reference characters are used throughout to designate like parts:

FIG. 1 is a perspective view of a device to close a wound on a patient constructed according to the present invention;

FIG. 2 is a perspective view of the device shown in FIG. 1 with the edges of the wound secured in close juxtaposition with one another and the securing portion of the device adhered to the patient;

FIG. 3 is a perspective view of the device shown in FIG. 2 with a sheet of protective material removed from the device shown in FIG. 1; and FIG. 4 is a perspective view of the device shown in FIG. 3 with the viewing portion of the device secured to the patient and the securing portion of the device.

BEST MODE FOR CARRYING OUT THE INVENTION

Turning now to FIGS. 1–4, there is shown a unitary wound closure device 10 adapted to permit a wound 12 on a patient 14 to be viewed while closure device 10 is secured to patient 14.

Device 10 comprises a body 16 having sufficient flexibility for it to be folded against itself, as best seen in FIG. 4.

Body 16 is made from a transparent plastic membrane and includes a first surface 18 and a second surface 20 facing away from surface 18.

As shown in FIGS. 2–4, a securing portion 22 is provided in body 16 and has a length 24 and a width 26 sufficient to secure facing edges 28 and 30 of wound 12 in close juxtaposition with one another. It has been found that when securing portion 22 has a width sufficiently small to permit viewing each side of the wound, wound closing device 10 works well by giving assurance to the viewer that he or she can see the ends of wound 12.

A viewing portion 32 is provided in body 16 and has a length 34 and width 36 sufficient to circumscribe wound 12 on patient 14. To permit observation of wound 12 in patient 14 and securing portion 22 on body 16, a window 38 is provided and is circumscribed by a framing border 40.

Body 16, preferably, appears in the general shape of a miniature tennis racket. Viewing portion 32 is in the general configuration of an oval member to resemble the racket portion of the tennis racket and securing portion 22 is in the general configuration of an elongated member to resemble the handle portion of the tennis racket. The oval member permits bedding to be slipped over device 10 without snagging. The elongated member is of such size as to permit relatively easy viewing of edges 28 and 30 of wound 12 and of such strength as to retain edges 28 and 30 of wound 12 in close juxtaposition.

A first quantity of adhesive substance 42 is disposed on first surface 18 of body 16 to adhere securing portion 22 of body 16 to patient 14.

A second quantity of adhesive substance 44 is disposed on second surface 20 of body 16 and border 40 to adhere viewing portion 32 to patient 14 and further secure portion 22 when viewing portion 32 is folded over and onto securing portion 22 and patient 14.

A first sheet of protective material 46 covers a first quantity of adhesive substance 42. First sheet 46 has a width at least as wide as width 26 of securing portion 22 and a length longer than length 24 to provide a lip 48, which extends beyond first quantity of adhesive substance 42 by a distance sufficient to allow lip 48 to be gripped by a finger and thumb encased within a rubber glove.

A second sheet of protective material 50 covers a second quantity of adhesive substance 44. Second sheet 50 has a width at least as wide as width 36 of viewing portion 32 and a length longer than length 34 to provide a lid 52, which extends beyond second quantity of adhesive substance 44 by a distance sufficient to allow lip 52 to be gripped by a finger and thumb encased within a rubber glove.

It has been found desirable to increase the stability of viewing portion 32 after second sheet 48 is removed from membrane of body 16 by making the border from a relatively inflexible material that is sufficiently inflexible to provide the desired stiffness while be sufficiently flexible to conform to the contours of patient 14, such as spun bonded Nylon.

In operation, a health care provider positions patient 14 with wound 12 at a convenient position to secure edges 28 and 30 together. While edge 28 and 30 are positioned close to one another, lip 48 of first protective sheet 46 is grasped between a finger and thumb encased within a rubber glove of the health care provider and protective sheet 46 removed from securing portion 22. Securing portion 22 is then secured on patient 14 as shown in FIG. 2 so that edges 28 and 30 are secured in close juxtaposition with one another. Then, as shown in FIG. 3, lip 52 of second protective sheet 50 is grasped between a finger and thumb encased within a rubber glove of the health care provider and protective sheet 50 removed from viewing portion 32. Viewing portion 32 is then folded over securing portion 22 and secured to securing portion 22 and patient 14, as shown in FIG. 4. After being secured to patient 14, the health care provider can see wound 12 to determine the status of the healing process or whether infection is developing.

The invention having been described, what is claimed is:

1. A unitary wound closure device adapted to permit a wound on a patient to be viewed while the closure device is secured to the patient, comprising:

a body having sufficient flexibility for it to be folded against itself, said body including first and second surfaces facing away from one another, a securing portion having a length and width sufficient to secure facing edges of the wound in close juxtaposition with one another, and a viewing portion having a length and width sufficient to circumscribe the wound on the patient;

the first surface forming an integral part of the securing portion;

a first quantity of adhesive substance disposed on the first surface of said body to adhere the securing portion of said body to the patient with the facing edges of the wound in said close juxtaposition; and a second quantity of adhesive substance disposed on the second surface of said body to adhere the viewing portion to the patient after securing the facing edge of the wound in said close juxtaposition, such that when the viewing portion is folded over and onto the securing portion and the patient, the wound and the securing portion are located beneath the viewing portion.

2. A device as set forth in claim 1, further comprising: said body further including the securing portion having a width sufficiently small to permit viewing each end of the wound.

3. A device as set forth in claim 1, further comprising: a first sheet of protective material to cover the first quantity of adhesive substance; and a second sheet of protective material to cover the second quantity of adhesive substance.

4. A device as set forth in claim 3, further comprising: the first sheet including a lip extending beyond the first quantity of adhesive substance by a distance sufficient to allow the lip to be gripped by a finger and thumb encased within a rubber glove; and the second sheet including a lip extending beyond the second quantity of adhesive substance by a distance sufficient to allow the lip to be gripped by a finger and thumb encased within a rubber glove.

5. A device as set forth in claim 1, further comprising: the viewing portion of said body further including a window for observing the wound on the patient and the securing portion on said body and a border circumscribing the window.

6. A unitary wound closure device adapted to permit a wound on a patient to be viewed while the closure device is secured to the patient, comprising:

a body having sufficient flexibility for it to be folded against itself, said body including first and second surfaces facing away from one another, a securing portion having a length and width sufficient to secure facing edges of the wound in close juxtaposition with one another, and a viewing portion having a length and width sufficient to circumscribe the wound on the patient;

a first quantity of adhesive substance disposed on the first surface of said body to adhere the securing portion of said body to the patient;

a second quantity of adhesive substance disposed on the second surface of said body to adhere the viewing portion to the patient, such that when the viewing portion is folded over and onto the securing portion and the patient, the wound and securing portion are located beneath the viewing portion;

said body further including the viewing portion being made from a transparent material through which the wound of the patient and the securing portion of said body may be viewed; and said second quantity of adhesive substance being made from a transparent material.

7. A unitary wound closure device adapted to permit a wound on a patient to be viewed while the closure device is secured to the patient, comprising:

a body having sufficient flexibility for it to be folded against itself, said body including first and second surfaces facing away from one another, a securing portion having a length and width sufficient to secure facing edges of the wound in close juxtaposition with one another, and a viewing portion having a length and width sufficient to circumscribe the wound on the patient;

a first quantity of adhesive substance disposed on the first surface of said body to adhere the securing portion of said body to the patient;

a second quantity of adhesive substance disposed on the second surface of said body to adhere the viewing portion to the patient, such that when the viewing portion is folded over and onto the securing portion and the patient, the wound and securing portion are located beneath the viewing portion; and said body further being disposed in the general shape of a miniature tennis racket, the securing portion being in the general configuration of an elongated member to resemble a handle portion of the tennis racket shape and the viewing portion being in the general configuration of an oval to resemble a racket portion of the tennis racket shape.

8. A unitary wound closure device adapted to permit a wound on a patient to be viewed while the closure device is secured to the patient, comprising: a body having sufficient flexibility for it to be folded against itself, said body including first and second surfaces facing away from one another, a securing portion having a length and width sufficient to secure facing edges of the wound in close juxtaposition with one another, and a viewing portion having a length and width sufficient to circumscribe the wound on the patient-;said body further including the viewing portion being made from a transparent material through which the wound of the patient and the securing portion of said body may be viewed; said body further being disposed in the general shape of a miniature tennis racket, the securing portion being in the general configuration of an elongated member to resemble a handle portion of the tennis racket shape and the viewing portion being in the general configuration of an oval to resemble a racket portion of the tennis racket shape; a first quantity of adhesive substance disposed on the first surface of said body to adhere the securing portion of said body to the patient; and a second quantity of adhesive substance disposed on the second surface of said body to adhere the viewing portion to the patient, such that when the viewing portion is folded over and onto the securing portion and the patient, the wound and securing portion are located beneath the viewing portion.

9. A device as set forth in claim 8, further comprising: a first sheet of protective material to cover the first quantity of adhesive substance; and a second sheet of protective material to cover the second quantity of adhesive substance.

10. A device as set forth in claim 9, further comprising: the first sheet including a lip extending beyond the first quantity of adhesive substance by a distance sufficient to allow the lip to be gripped by a finger and thumb encased within a rubber glove; and the second sheet including a lip extending beyond the second quantity of adhesive substance by a distance sufficient to allow the lip to be gripped by a finger and thumb encased within a rubber glove.

11. A unitary wound closure device adapted to permit a wound on a patient to be viewed while the closure device is secured to the patient, comprising: a body having sufficient flexibility for it to be folded against itself, said body including first and second surfaces facing away from one another, a securing portion having a length and width sufficient to secure facing edges of the wound in close juxtaposition with one another, and a viewing portion having a length and width sufficient to circumscribe the wound on the patient; the viewing portion of said body further including a window for observing the wound on the patient and the securing portion on said body and a border circumscribing the window, the border being made from a relatively inflexible material that is sufficiently inflexible to provide the desired stiffness while being sufficiently flexible to conform to the contours of the patient; a first quantity of adhesive substance disposed on the first surface of said body to adhere the securing portion of said body to the patient; and a second quantity of adhesive substance disposed on the second surface of said body to adhere the viewing portion to the patient, such that when the viewing portion is folded over and onto the securing portion and the patient, the wound and securing portion are located beneath the viewing portion.

12. A unitary wound closure device adapted to permit a wound on a patient to be viewed while the closure device is secured to the patient, comprising: a body having sufficient flexibility for it to be folded against itself, said body including first and second surfaces facing away from one another, a securing portion having a length and width sufficient to secure facing edges of the wound in close juxtaposition with one another, and a viewing portion having a length and width sufficient to circumscribe the wound on the patient, a window for observing the wound on the patient and the securing portion on said body and a border circumscribing the window, the border being made from a relatively inflexible material that is sufficiently inflexible to provide the desired stiffness while being sufficiently flexible to conform to the contours of the patient, said body further being disposed in the general shape of a tennis racket, the viewing portion being in the general configuration of an oval to resemble the racket portion of the tennis racket and the securing portion being in the general configuration of an elongated member to resemble the handle portion of the tennis racket, said body further including the viewing portion being made from a transparent material through which the wound on the patient and the securing portion on said body may be viewed; a first quantity of adhesive substance disposed on the first surface of said body to adhere the securing portion of said body to the patient; a second quantity of adhesive substance disposed on the second surface of said body to adhere the viewing portion to the patient and the securing portion when the viewing portion is folded over and onto the securing portion and the patient: a first sheet of protective material to cover the first quantity of adhesive substance, the first sheet including a lip extending beyond the first quantity of adhesive substance by a distance sufficient to allow the lip to be gripped by a finger and thumb encased within a rubber glove; and a second sheet of protective material to cover the second quantity of adhesive substance, the second sheet including a lip extending beyond the second quantity of adhesive substance by a distance sufficient to allow the lip to be gripped by a finger and thumb encased within a rubber glove.

13. A method of protecting and viewing a wound in a patient, comprising the steps of: positioning the edges of the wound in close juxtaposition relation to one another; adhering a securing portion of a flexible material over the wound of the patient to secure the edges of the wound in close juxtaposition; folding a viewing portion of the flexible material over the securing portion of the flexible material; and adhering the viewing portion of the flexible material to the patient and the securing portion of the flexible material.

14. A method as set forth in claim 13, further comprising the steps of: grasping a lip on a first sheet of protective material that is disposed on a first quantity of adhesive substance provided on the securing portion of the flexible material; removing the first sheet of protective material from the first quantity of adhesive substance prior to securing the securing portion of the flexible material to the patient; grasping a lip on a second sheet of protective material that is disposed on a second quantity of adhesive substance provided on the viewing portion of the flexible material; and removing the second sheet of protective material from the second quantity of adhesive substance prior to securing the viewing portion of the flexible material to the securing portion of the flexible material.

* * * * *